United States Patent [19]

Smith et al.

[11] Patent Number: 5,389,685
[45] Date of Patent: Feb. 14, 1995

[54] STABILIZER DISINFECTANT FORMULATION

[75] Inventors: Kim Smith; Fred Boyd, both of Huntington, Ind.

[73] Assignee: Huntington Laboratories, Inc., Huntington, Ind.

[21] Appl. No.: 75,136

[22] Filed: Jun. 10, 1993

[51] Int. Cl.$^6$ .................. A01N 33/12; C11D 3/48
[52] U.S. Cl. .................. 514/643; 514/644; 514/642; 252/106; 252/107
[58] Field of Search ............ 514/643, 642, 644; 252/106, 107

[56] References Cited

U.S. PATENT DOCUMENTS

| | | | |
|---|---|---|---|
| 3,836,669 | 9/1974 | Dadekran | 514/642 |
| 3,892,669 | 8/1975 | Rapsisarda et al. | 252/8.75 |
| 4,464,398 | 8/1984 | Sheets et al. | 514/643 |

Primary Examiner—Glennon H. Hollrah
Assistant Examiner—Deborah Lambkin
Attorney, Agent, or Firm—Barnes & Thornburg

[57] ABSTRACT

The color-stability of disinfectant formulations comprising bacteriocidal quaternary amine compounds, a non-ionic surfactant, and water is enhanced significantly by adding color-stabilizing amounts of an alkali bicarbonate. An alkali bicarbonate can be used in lieu of the art-accepted EDTA/NaOH builder in quaternary amine-based disinfectant formulations to enhance color stability without sacrificing the bacteriocidal efficacy of the formulations.

9 Claims, No Drawings

STABILIZER DISINFECTANT FORMULATION

FIELD OF THE INVENTION

The present invention relates to quaternary amine-based disinfectant formulations. More particularly it is directed to an improved disinfectant formulation which exhibits exceptional resistance to the art-recognized time/temperature dependent discoloration of state-of-the-art quaternary amine-based disinfectants.

BACKGROUND AND SUMMARY OF THE INVENTION

Many commercial operations, including restaurants, nursing homes, hospitals, and laboratories, utilize large amounts of hard surface disinfectants and typically maintain a significant inventory of such products. As a consequence of that and the fact that commercial disinfectants are often manufactured and sold in large quantities, disinfectant products are often stored for long periods of time. They are stored in warehouses before they are shipped to customers and then they are stored again as part of the customer's inventory. Because it is known that certain quaternary amine-based disinfectant formulations tend to discolor (turn yellow) over time, and because customers expect (and demand) product stability, research efforts have been focused on development of a stabilized disinfectant composition which maintains its clarity and does not discolor during storage.

A number of researchers have focused on the use of didecyl dimethyl ammonium chloride and quaternary ammonium chlorides for use in germicidal compositions. See for example U.S. Pat. No. 3,836,669, and Kirk-Othmer Encyclopedia of Chemical Technology. The compositions, however, required the addition of ammonium sulfate to give the composition the clarity of water. They gained only limited acceptance in the market-place due to the noticeable ammonia smell left behind long after the composition was applied. Recognition of the market's desire for water-clarity along with the high volume use of hard surface disinfectants has provided significant incentive to develop water-clear disinfectant solutions lacking an offensive ammonia smell.

More recently other researchers have reported that water-clear germicidal compositions could be formulated without the addition of ammonium sulphate and with the addition of tetrasodium ethylenediamine tetraacetate. See for example U.S. Pat. No. 4,464,398. The tetrasodium ethylenediaminetetraacetate serves as a detergent builder. Further, tetrasodium ethylenediamine tetraacetate has been considered to be a necessary component of the formulation for its function to aid in the breaking down of the bacterial cell walls. Quaternary amine-based disinfectant compositions utilizing ethylenediamine tetraacetic acid ("EDTA") and sodium hydroxide, however, fail to maintain their clarity, and often discolor with or without the addition of dyes during storage. There remains, therefore, a significant need to develop a clear, color-stable, hard surface disinfectant which provides both the performance and appearance properties necessary to meet customer expectations.

According to the present invention, there is provided a disinfectant composition formulated to have improved color stability without compromising bacteriocidal activity. The composition comprises bacteriocidal quaternary amine compounds a non-ionic surfactant, water, and an alkali bicarbonate in an amount effective to retard discoloration of the composition.

Further in accordance with this invention there is provided a method for improving stability of quaternary amine-based disinfectant compositions by the addition of effective amounts of alkali bicarbonates.

Additional objects, features, and advantages of the invention will become apparent to those skilled in the art upon consideration of the following detailed description of the preferred embodiments exemplifying the best mode of carrying out the invention.

DETAILED DESCRIPTION OF THE INVENTION

In accordance with the present invention there is provided a method for reducing, even eliminating, discoloration of quaternary amine-based disinfectant compositions during storage—a problem that has been noted particularly with respect to such formulations containing ethylenediaminetetraacetic acid (EDTA) sodium salts. It has been found that an alkali bicarbonate can be used in lieu of EDTA salts (EDTA+sodium hydroxide) to enhance the color stability of the compositions without compromising bacteriocidal efficacy. Thus, in accordance with one embodiment of this invention, there is provided a method for enhancing the color stability of a water-dispersible disinfectant formulation comprising bacteriocidal quaternary amine compounds, a non-ionic surfactant and water. The method includes the step of adding to the formulation about 0.01 to about 1 percent by weight of an alkali bicarbonate. The color stable hard surface disinfectant formulations of the present invention comprise bacteriocidal quaternary amine compounds, a non-ionic surfactant, particularly an alkyldimethylamine oxide, water, and an alkali bicarbonate in an amount effective to retard the discoloration of the disinfectant formulation during storage. The preferred compositions of this invention differ from present commercially available disinfectant compositions particularly in that they utilize an alkali bicarbonate in lieu of the standard art-accepted builder—ethylenediaminetetraacetic acid sodium salt, formed in such mixtures typically by the addition of EDTA and sodium hydroxide. Thus in a preferred embodiment the compositions of the color-stabilized present invention are substantially free of EDTA sodium salts. The compositions of the present invention, like those compositions which have been commercially available, can include other optional ingredients such as fragrance oils or dyes to enhance customer acceptance of the product.

One preferred group of quaternary amine-based bacteriocidal compositions which can be modified and color stabilized in accordance with the present invention are those described in U.S. Pat. No. 4,464,398, issued Aug. 7, 1984, the disclosure of which is expressly incorporated herein by reference.

The nature of the bacteriocidal quaternary amine compounds utilized in the color stable compositions of the present invention are not critical so long as the compounds have the requisite bacteriocidal functionality. Many quaternary amine compounds are known to exhibit germicidal activity against a wide variety of microorganisms. One group of preferred quaternary amine compounds that can be utilized as a bacteriocidal component of the present compositions are those designated alkyldimethylbenzylammonium halides of the formula $$R^1N^+(CH_3)_2(CH_2C_6H_6) \ X^-$$

wherein $R^1$ is a $C_8$–$C_{24}$ alkyl group and X is Cl, Br, I, or F. Another group of bacteriocidal quaternary ammonium compounds which find use in the present color stable formulations are designated generally as dialkyldimethylammonium halides of the formula $$R^2N^+(R^3) \ (CH_3)_2 \ X^{31}$$

wherein $R^2$ and $R^3$ are each independently $C_8$–$C_{24}$ alkyl and X is as defined above. Commercially available alkyldimethylbenzylammonium halide compositions typically include a mixture of such compounds wherein the alkyl component includes $C_{12}$-alkyl, $C_{14}$-alkyl, and $C_{16}$-alkyl substituents. In the most preferred color stable formulations of the present invention, the bacteriocidal quaternary amine component includes about 1 to about 12 percent, more preferably about 3 to about 9 percent, most preferably about 5 to about 7 percent of an alkyldimethylbenzylammonium halide and about 1 to about 18 percent, more preferably about 6 to about 12 percent, and most preferably about 8 to about 10 percent by weight of a dialkyldimethylammonium halide.

The non-ionic surfactant component of the present color stable formulations can be selected from a wide variety of art-recognized non-ionic surfactant compositions. Thus the non-ionic surfactant component of the present formulation can be selected from monoethers of polyglycols with long-chain fatty alcohols, monoesters of polyglycols with long-chain fatty acids, monoethers of polyglycols with alkylated phenols, polyoxyethylene sorbitan fatty and/or resin acid esters, N,N-polyethoxylates and polypropoxylates of long-chain aliphatic amines, and alkyldimethylamine oxides. One preferred non-ionic surfactant composition for use in the present color stabilized formulation is an alkyldimethylamine oxide of the formula $R^4N(CH_3)_2(O)$ wherein $R^4$ is $C_8$–$C_{24}$ alkyl. Non-ionic surfactants can be used alone or in combination. The surfactant component typically comprises about 1 to about 10 weight percent, more typically from about 1 to about 6 weight percent, and most preferably from about 2 to about 4 weight percent of the formulation.

Suitable alkali bicarbonates for use in accordance with this invention include alkali bicarbonates of the formula $M^{+a}(HCO_3)_a$ wherein M is Na, K, $NH_4$, Ca, Mg, and wherein a is 1 or 2, dependent on the valance of the cation specified. The alkali bicarbonate is added to the formulation in an amount sufficient to retard the time/temperature dependent discoloration of the disinfectant formulation. Generally the amount of alkali bicarbonate effective to stabilize the formulation is about 0.1 to about 1 weight percent, more typically about 0.05 to about 0.5 weight percent, and most preferably about 0.1 to about 0.2 weight percent of the bacteriocidal formulation. The exact mechanism of the color stabilizing efficacy of the alkali bicarbonate has not been determined, however its addition to the formulation does affect, and indeed buffer, the pH of the formulation. Generally the pH range of the formulated color stable product is about 6.5 to about 8.5.

Other ingredients which can be added to the present compositions to enhance product acceptability include fragrance, typically in the form of fragrance oil concentrates, and dyes. Thus the stabilized disinfectant formulations of the present invention can contain from about 0 to about 3 percent, more typically from about 0.1 to about 1 weight percent, and most preferably from about 0.3 to about 0.7 weight percent of a dye and about 0 to about 3 weight percent, more preferably from about 0.5 to about 1 weight percent, and most preferably about 0.3 to about 0.7 weight percent of a fragrance component.

The present disinfectant formulations also include about 53 to about 97 weight percent water. The composition is typically detailed for use by further dilution with water to provide a cleaning solution containing about 50 to about 3000 ppm bacteriocidal quaternary amine compounds.

The germicidal activity of the color-stabilized formulations of the present invention was determined to be equivalent to the activities of EDTA/sodium salt containing reported in U.S. Pat. No. 4,464,398 against *Pseudomonas aeruginosa*, *Staphyloccus aureus*, and *Salmonella choleraesuis* as measured by the AOAC Use-Dilution test in the presence of 400 ppm $CaCO_3$, synthetic hard water, and 5% serum.

EXAMPLE I

A disinfectant formulation having the following formula was prepared as a hard surface disinfectant.

| FORMULATION | |
| --- | --- |
| FMB 1210-8* (80% active) | 76.84 g |
| FMB AO-8** (40% active) | 32.00 g |
| Water | 290.66 g |
| Sodium bicarbonate | 0.50 g |

The pH of the resulting formulation was 7.4–7.5, and the percentage quaternary amine in the resulting formulation was 15.845%. After 30 days the solution remained clear, and it exhibited no color change.

| | |
| --- | --- |
| *FMB 1210-8 | |
| didecyldimethylammonium chloride | 60% |
| alkyldimethylbenzylammonium chloride | 40% (40% $C_{12}$, 50% $C_{14}$, and 10% $C_{16}$) |
| **FMB AO-8 | |
| octyldimethylamine oxide | |

EXAMPLE II

A disinfectant formulation having the following formula is prepared as a hard surface disinfectant.

| FORMULATION | |
| --- | --- |
| alkyldimethylbenzylammonium halide | 6% |
| dialkyldimethylammonium halide | 9% |
| alkyldimethylamine oxide | 3% |
| sodium bicarbonate | 0.1% |
| fragrance | % as desired |
| dye | % as desired |
| water | q.s. to 100%. |

EXAMPLE III

Color-stable disinfectant formulations having the following formulas are prepared as a hard surface disinfectants.

| FORMULATIONS | | | |
| --- | --- | --- | --- |
| alkyldimethylbenzyl- | 6% | 17% | — |

| FORMULATIONS -continued | | | |
|---|---|---|---|
| ammonium halide | | | |
| dialkyldimethylammonium halide | 9% | — | 14% |
| linear primary ethoxylated alcohol | 3% | — | 3% |
| alkyldimethylamine oxide | 3% | 10% | — |
| alkali bicarbonate | 0.1% | .8% | 1% |
| fragrance | % desired | % desired | % desired |
| dye | % desired | % desired | % desired |
| water | qs to 100% | qs to 100% | qs to 100% |

Although the invention has been described in detail with reference to certain preferred embodiments, variations and modifications exist within the scope and spirit of the invention as described and defined in the following claims.

We claim:

1. A color-stable hard surface disinfectant formulation comprising about 2 to about 30 weight percent of bacteriocidal quaternary amine compounds,
   about 1 to about 10 weight percent of a ($C_8$–$C_{24}$ alkyl) dimethylamine oxide,
   water, and
   an alkali bicarbonate in an amount effective to retard the discoloration of the disinfectant formulation during storage.

2. The color-stable formulation of claim 1 having a pH in the range of about 6.5 to about 8.5.

3. The color-stable formulation of claim 1 wherein the formulation is substantially free of sodium hydroxide and ethylenediaminetetraacetic acid.

4. The color-stable formulation of claim 1 wherein the bacteriocidal quaternary amine compounds comprise a ($C_8$–$C_{\geq}$alkyl)dimethylbenzylammonium halide and a dialkyldimethylammonium halide of the formula $R^2N^+(CH_3)_2(R_3)X^-$ wherein $R^2$ and $R^3$ are independently $C_8$–$C_{24}$ alkyl.

5. A clarity/color-stable hard surface disinfectant formulation comprising
   about 2 to about 30 weight percent bacteriocidal quaternary amine compounds,
   about 1 to about 10 weight percent of a ($C_8$–$C_{24}$ alkyl) dimethylamine oxide,
   water, and
   about 0.01 to about 1 weight percent of an alkali bicarbonate.

6. The color-stable formulation of claim 5 having a pH in the range of about 6.5 to about 8.5.

7. The color-stable formulation of claim 5 wherein the formulation is substantially free of sodium hydroxide and ethylenediaminetetraacetic acid.

8. The color-stable formulation of claim 5 wherein the bacteriocidal quaternary amine compounds comprise a ($C_8$–$C_{24}$ alkyl)dimethylbenzylammonium halide and a dialkyldimethylammonium halide of the formula $R^2N^+(CH_3)_2(R^3)X^-$ wherein $R^2$ and $R^3$ are independently $C_8$–$C_{24}$ alkyl.

9. A method for enhancing the color stability of a water-dispersible formulation comprising bacteriocidal quaternary amine compounds, a ($C_8$–$C_{24}$ alkyl) dimethylamine oxide and water, said method comprising the step of adding to said formulation about 0.01 to about 1 percent by weight of an alkali bicarbonate.

* * * * *